(12) United States Patent
Foster et al.

(10) Patent No.: US 8,275,468 B2
(45) Date of Patent: Sep. 25, 2012

(54) HELICAL FIXATION MEMBER WITH CHEMICAL ELUTION CAPABILITIES

(75) Inventors: Arthur J. Foster, Centerville, MN (US); Matthew J. Miller, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 124 days.

(21) Appl. No.: 12/490,015

(22) Filed: Jun. 23, 2009

(65) Prior Publication Data
US 2010/0004723 A1 Jan. 7, 2010

Related U.S. Application Data

(60) Provisional application No. 61/077,939, filed on Jul. 3, 2008.

(51) Int. Cl.
*A61N 1/00* (2006.01)
(52) U.S. Cl. ........................................ 607/120; 607/127
(58) Field of Classification Search .................. 607/120, 607/127, 131
See application file for complete search history.

(56) References Cited

U.S. PATENT DOCUMENTS

| | | | |
|---|---|---|---|
| 4,506,680 A | 3/1985 | Stokes | |
| 4,577,642 A | 3/1986 | Stokes | |
| 4,606,118 A | 8/1986 | Cannon et al. | |
| H356 H | 11/1987 | Stokes et al. | |
| 4,711,251 A | 12/1987 | Stokes | |
| 4,784,161 A | 11/1988 | Skalsky et al. | |
| 4,819,661 A | 4/1989 | Heil, Jr. et al. | |
| 4,844,099 A | 7/1989 | Skalsky et al. | |
| 4,866,074 A | 9/1989 | Spada et al. | |
| 4,886,074 A | 12/1989 | Bisping | |
| 4,953,564 A | 9/1990 | Berthelsen | |
| 5,002,067 A | 3/1991 | Berthelsen et al. | |
| 5,282,844 A | 2/1994 | Stokes et al. | |
| 5,324,324 A | 6/1994 | Vachon et al. | |
| 5,324,325 A | 6/1994 | Moaddeb | |
| 5,405,376 A | 4/1995 | Mulier et al. | |
| 5,551,426 A | 9/1996 | Hummel et al. | |
| 5,833,715 A | 11/1998 | Vachon et al. | |
| 6,086,582 A | 7/2000 | Altman et al. | |
| 6,102,887 A | 8/2000 | Altman | |
| 6,346,099 B1 | 2/2002 | Altman | |
| 6,478,776 B1 * | 11/2002 | Rosenman et al. | 604/164.01 |
| 6,547,787 B1 * | 4/2003 | Altman et al. | 606/41 |

(Continued)

FOREIGN PATENT DOCUMENTS
WO WO 03/092799 11/2003

OTHER PUBLICATIONS
International Search Report and Written Opinion issued in PCT/US2009/048266, mailed Sep. 3, 2009, 12 pages.

(Continued)

*Primary Examiner* — Mark W Bockelman
(74) *Attorney, Agent, or Firm* — Faegre Baker Daniels LLP

(57) ABSTRACT

The lead includes a helical fixation member coupled to the distal end of the lead body. The helical fixation member has at least one internal reservoir and a plurality of elution ports in fluid communication with the internal reservoir. A therapeutic agent composition is disposed within the internal reservoir. Additionally, the helical fixation member includes a sealed distal end to prevent coring of the cardiac tissue.

15 Claims, 5 Drawing Sheets

U.S. PATENT DOCUMENTS

| | | | |
|---|---|---|---|
| 6,569,144 B2 | 5/2003 | Altman | |
| 6,855,160 B1 | 2/2005 | Gambale et al. | |
| 7,103,418 B2 | 9/2006 | Laske et al. | |
| 7,155,292 B2 | 12/2006 | Kawula et al. | |
| 7,158,837 B2 | 1/2007 | Osypka et al. | |
| 7,187,971 B2 | 3/2007 | Sommer et al. | |
| 7,197,362 B2 | 3/2007 | Westlund | |
| 7,274,966 B2 | 9/2007 | Sommer et al. | |
| 7,363,091 B1 | 4/2008 | Chen et al. | |
| 7,369,901 B1 | 5/2008 | Morgan et al. | |
| 7,500,970 B2 | 3/2009 | Altman | |
| 2002/0045926 A1 | 4/2002 | Heil et al. | |
| 2004/0024371 A1 | 2/2004 | Plicchi et al. | |
| 2004/0068299 A1 | 4/2004 | Laske et al. | |
| 2004/0068312 A1 | 4/2004 | Sigg et al. | |
| 2005/0070988 A1 | 3/2005 | Kawula et al. | |
| 2006/0235499 A1 | 10/2006 | Heil, Jr. et al. | |

OTHER PUBLICATIONS

Stokes, Kenneth B., "Preliminary Studies on a New Sterioid Eluting Epicardial Electrode", PACE, vol. 11, Nov. 1988, Part II, pp. 1797-1803.

* cited by examiner

PROVIDE A CARDIAC PACING THERAPY SYSTEM INCLUDING A PULSE GENERATOR AND A LEAD, THE LEAD INCLUDING A HELICAL FIXATION MECHANISM WITH AN INTERNAL RESERVOIR AND AT LEAST ONE ELUTION PORT IN FLUID COMMUNICATION WITH THE INTERNAL RESERVOIR

AFFIXING THE HELICAL FIXATION ELECTRODE TO A MYOCARDIUM OF THE HEART SUCH THAT THE ELUTION PORTS ARE IN CLOSE PROXIMITY TO THE MYOCARDIUM

APPLYING PACING THERAPY TO THE PATIENT'S HEART WITH THE PACING THERAPY SYSTEM

FIG.7

HELICAL FIXATION MEMBER WITH CHEMICAL ELUTION CAPABILITIES

CROSS-REFERENCE TO RELATED APPLICATION

This application claims the benefit under 35 U.S.C §119 of U.S. Provisional Application No. 61/077,939, filed on Jul. 3, 2008, entitled "Helical Fixation Mechanism with Chemical Elution Capabilities," which is herein incorporated by reference in its entirety.

TECHNICAL FIELD

The present invention relates to cardiac rhythm management systems, and in particular to mechanisms for improving the performance of cardiac leads implanted in a patient's vascular system.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One manner of treating cardiac arrhythmias includes the use of a cardiac rhythm management system. Such systems can be implanted in a patient to deliver electrical pulses to the heart.

Cardiac rhythm management systems include, for example, pacemakers (also referred to as "pacers"), defibrillators (also referred to as "cardioverters") and cardiac resynchronization therapy ("CRT") devices. These systems use conductive leads having one or more electrodes to deliver pulsing energy to the heart, and can be delivered to an endocardial, epicardial and myocardial position within the heart.

Unfortunately, interactions between the electrode and the adjacent tissue in the heart may vary the stimulation thresholds of the tissue over time. This variation can be caused by the formation of fibrotic scar tissue during the recovery and healing process as the body reacts to the presence of the electrode. The formation of fibrotic tissue may result in chronic stimulation energy thresholds that exceed the acute energy thresholds obtained immediately after implant. As a result, higher stimulation energies are required, thereby shortening the usable life of the battery-powered implantable cardiac rhythm management device.

To inhibit the growth of scar tissue, leads have been configured to release active agents such as steroids in the vicinity of the electrode. For example, drug eluting collars have been placed adjacent to electrodes to inhibit the growth of scar tissue. One challenge with drug eluting collars and other drug release structures is that it is difficult to control both the amount of drug being released and the amount of drug that ultimately reaches the affected tissue site.

SUMMARY

In one embodiment, a medical electrical lead includes a helical fixation member including at least a first internal reservoir, a plurality of elution ports located along a length of the helical fixation member in fluid communication with the first internal reservoir, and a sealed distal tip configured to engage the cardiac tissue at the implantation site. A first therapeutic agent composition including at least one therapeutic agent and a carrier is disposed and contained within the first internal reservoir.

In another embodiment, a medical electrical lead includes a helical fixation member having a first internal reservoir including a first therapeutic agent composition disposed therein, a second internal reservoir having a second therapeutic agent composition disposed therein and a plurality of elution portions located along a length of the helical fixation member comprising a first plurality of ports in fluid communication with the first internal reservoir and a second plurality of ports in fluid communication with the second internal reservoir.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 7 is a flow-chart summarizing a method of using embodiments of the present invention.

Figure 1:
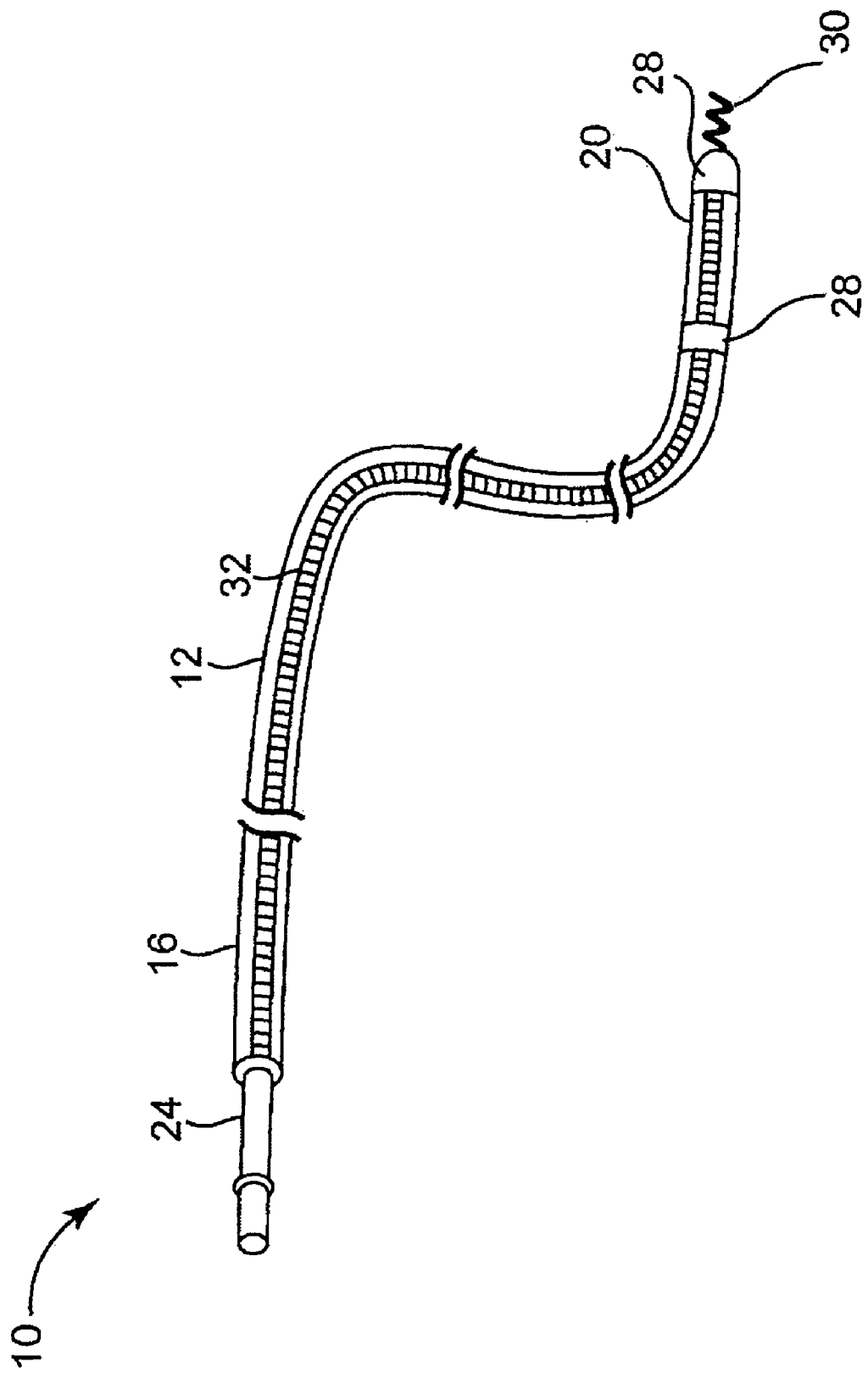
FIG. 1 is a partial cross-sectional view of a medical electrical lead according to various embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a partial cross-sectional view of a medical electrical lead 10, according to various embodiments of the present invention. According to some embodiments, the medical electrical lead 10 can be configured for implantation within a patient's heart. According to other embodiments, the medical electrical lead 10 is configured for implantation within a patient's neurovascular regions. The medical electrical lead 10 includes an elongated, insulative lead body 12 extending from a proximal end 16 to a distal end 20. The proximal end 16 is configured to be operatively connected to a pulse generator via a connector 24. At least one conductor 32 extends from the connector 24 at the proximal end 16 of the lead 10 to one or more electrodes 28 at the distal end 20 of the lead 10. The conductor 32 can be a coiled or cable conductor.

According to some embodiments where multiple conductors are employed, the lead can include a combination of coiled and cable conductors. When a coiled conductor is employed, according to some embodiments, the conductor can have either a co-radial or a co-axial configuration.

The lead body 12 is flexible, but substantially non-compressible along its length, and has a circular cross-section. According to one embodiment of the present invention, an outer diameter of the lead body 12 ranges from about 2 to about 15 French. The medical electrical lead 10 can be unipolar, bipolar, or multi-polar depending upon the type of therapy to be delivered. In embodiments of the present invention employing multiple electrodes 28 and multiple conductors 32, each conductor 32 is adapted to be connected to an individual electrode 28 in a one-to-one manner allowing each electrode 28 to be individually addressable.

Additionally, the lead body 12 can include one or more lumens. In some embodiments at least one lumen is adapted to receive the insertion of a conductor during construction of the medical electrical lead. In further embodiments, at least one lumen is adapted to receive a guiding element such as a guidewire or a stylet for delivery of the lead 10 to a target location within a patient's heart.

The electrodes 28 can have any electrode configuration as is known in the art. According to one embodiment of the present invention, at least one electrode can be a ring or partial ring electrode. According to another embodiment, at least one electrode 28 is a shocking coil. According to yet another embodiment of the present invention, at least one electrode 28 includes an exposed electrode portion and an insulated electrode portion. In some embodiments, a combination of electrode configurations can be used. The electrodes 28 can be coated with or formed from carbon, platinum, stainless steel, MP35N, a platinum-iridium alloy, or another similar conductive material. In further embodiments, a steroid eluting collar can be located adjacent to at least one electrode 28.

According to various embodiments, the lead body 12 includes a fixation member 30 for securing and stabilizing the lead body 12 including the one or more electrodes 28 at an implantation site within a patient's heart. In some embodiments, the fixation member 30 can be a screw-in fixation member. In other embodiments, the fixation member can be an extendable/retractable fixation member and can include one or more mechanical components adapted to facilitate the extension/retraction of the fixation member. Upon implantation of the lead, the fixation member 30 can be affixed directly into the myocardium or epicardium of a patient's heart.

Figure 2:
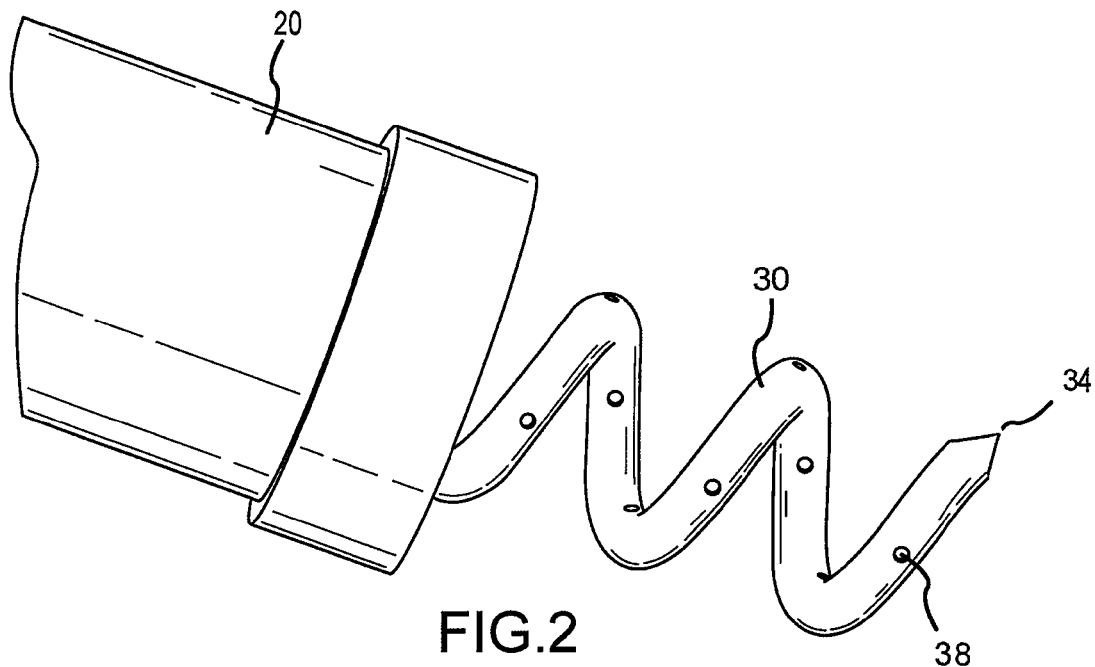
FIG. 2 is a schematic illustration of the distal end of a cardiac lead according to embodiments of the present invention.
Figure 3:
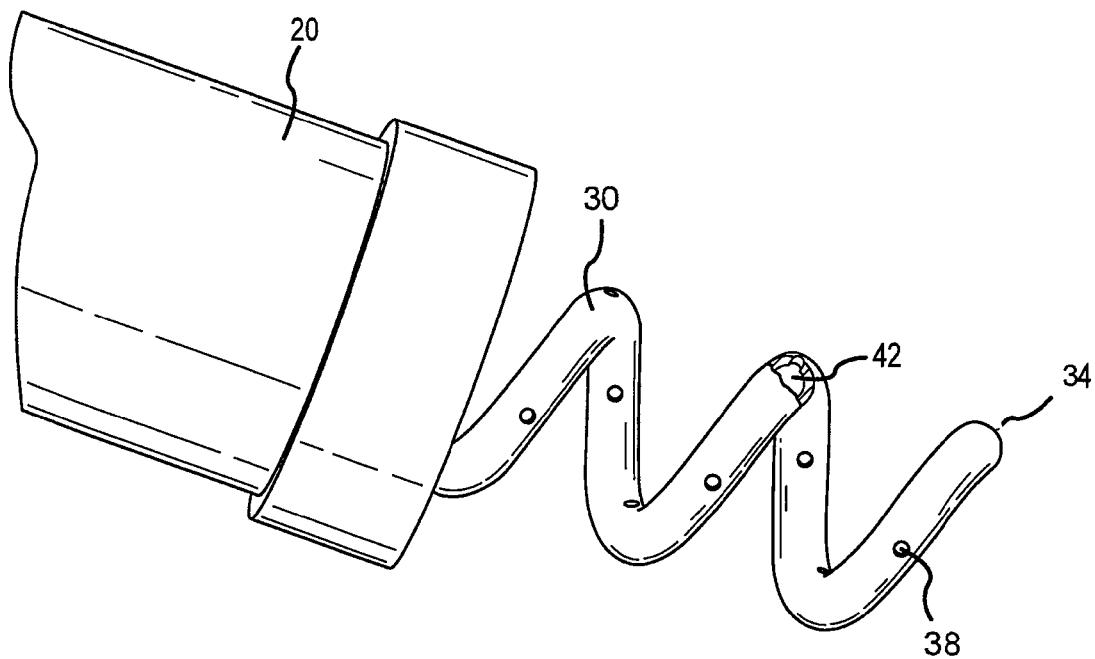
FIG. 3 is a schematic illustration of the distal end of a cardiac lead according to embodiments of the present invention.
Figure 4:
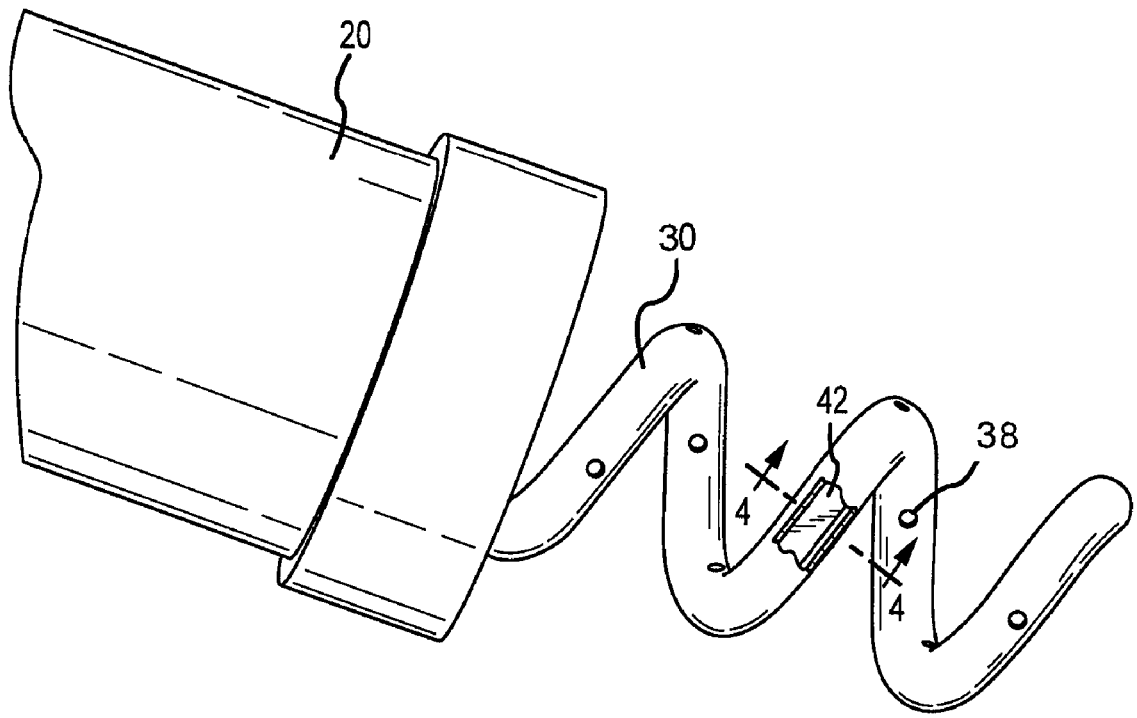
FIG. 4 is a schematic illustration of the distal end of a cardiac lead according to embodiments of the present invention.

FIGS. 2-4 show enlarged views of the distal end 20 of the lead 10 according to various embodiments of the present invention. As illustrated in FIGS. 2-4, the fixation member 30 is a helical fixation member and is coupled to the distal end 20 of the lead 10. The fixation member 30 can be fabricated from a variety of materials and can have an outer diameter ranging from about 1 to about 12 French. Exemplary materials suitable for the fabrication of the fixation member 30 include, but are not limited to: platinum, palladium, nickel-titanium alloys (e.g., Nitinol), stainless steel, polymer, and machined or cast ceramics. According to embodiments of the present invention, the fixation member 30 can be made out of a straight tube which can then be formed into a helix or other shape suitable for fixation.

According to some embodiments of the present invention, the fixation member 30 can be operatively coupled to the at least one conductor 32 such that it functions as an electrode. The fixation member 30 can be conductive and designed to be positively fixed to the desired site in the heart to deliver current to the heart for cardiac rhythm management therapy. According to other embodiments of the present invention, the fixation member 30 can be used primarily for fixation of the lead 10 to the desired site in the heart while cardiac rhythm management therapy current is applied from a portion of the lead 10 adjacent to the fixation member 30.

According to various embodiments, the helical fixation member 30 includes a distal tip 34 configured to engage the cardiac tissue at the implantation site. In one embodiment, the distal tip 34 is a sharpened distal tip 34 (FIG. 2). In further embodiments, the distal tip 34 is sealed and is impenetrable to the surrounding environment.

According to various embodiments, as illustrated in FIGS. 2-4, the fixation member 30 also includes one or more elution ports 38 in fluid communication with at least one internal reservoir 42 (FIGS. 3 & 4). According to embodiments of the present invention, a therapeutic agent is disposed in the internal reservoir 42 and elutes through the elution ports 38 into the surrounding cardiac tissue at the fixation site.

The elution ports 38 can be of various number, shapes and sizes, and can be spaced substantially evenly along the fixation member 30 or concentrated at one or more points on the fixation member 30. The size, shape, number, and spacing of the elution ports 38 can be varied depending on factors such as the type of therapeutic agent being used, the type of carrier being used, the desired release rate, and the time period for release of the therapeutic agent. The elution ports 38 can be formed in the fixation member 30 using a variety of fabrication techniques. For example, the elution ports 38 can be formed through various drilling means, by use of a laser, and/or by conventional etching techniques.

In various embodiments, the elution ports 38 are located along the length of the fixation member 30. While the elution ports can be located anywhere along the length of the fixation member 30, in one embodiment the fixation member 30 does not include an elution port 38 located at its distal tip 34. By providing elution ports 38 along the length of the fixation member 30 and not at its tip 34, coring of the cardiac tissue upon implantation of the fixation member 30 can be prevented. Any tissue trapped within the fixation member 30 resulting from coring of the cardiac tissue may adversely affect the elution of the therapeutic agent into the surrounding tissue.

FIG. 3 shows a cut away portion of the fixation member 30 exposing the internal reservoir 42 according to one embodiment of the present invention. For example, in one embodiment, the fixation member 30 is fabricated from a hollow helical tube where the hollow portion forms the internal reservoir 42. In another embodiment, the internal reservoir 42 is defined by bored out sections of an elongated member such as, for example, a wire used to form the fixation member 30.

A variety of therapeutic agents can be incorporated into the internal reservoir 42 to treat the tissue surrounding the fixation site of the fixation member 30 by providing an anti-inflammatory effect in order to maintain or reduce the chronic energy thresholds required to provide rhythm management therapy to the heart. Steroids are a broad class of therapeutic agents that are suitable for use in embodiments of the present invention. Examples of suitable steroids include, but are not limited to, the following: dexamethasone, betamethasone, paramethasone, beclomethasone, clobetasol, triamcinolone, prednisone, and prednisolone, as well as combinations and derivatives thereof. Suitable steroid derivatives include esters of steroids, such as the acetate, diacetate, propionate, dipropionate, cypropionate, butyrate, acetonide, hexacetonide, succinate, and valerate esters of such steroids. In some embodiments, the therapeutic agent includes the acetate esters of dexamethasone or beclomethasone. Beclomethasone dipropionate anhydrous may also be suitable for certain embodiments. In one embodiment the therapeutic agent includes dexamethasone or derivatives thereof. In another embodiment, the therapeutic agent includes beclomethasone or derivatives thereof. The therapeutic agent can also include a combination of steroids or other therapeutic agents. An additional class of therapeutic agents suitable for certain embodiments include anti-cell proliferation agents.

According to embodiments of the present invention, the therapeutic agent can be contained within a carrier disposed within the internal reservoir 42. A wide variety of liquid and solid carriers could be used. In one embodiment, the therapeutic agent is contained in a biocompatible liquid or gel polymer. The polymer material may remain within the internal reservoir 42 on the fixation member 30 for the life of the lead 10 or it can be partially or completely biodegradable over time. In a further embodiment, the polymer material may have a low water solubility or can be substantially water insoluble. According to embodiments of the present invention, suitable polymeric materials should also be compatible with the therapeutic agent with which the polymeric material is combined. Examples of suitable polymer materials include, but are not limited to: silicone rubbers, polyurethanes, polyesters, polylactic acids, polyamino acids, polyvinyl alcohols and polyethylenes.

The specific combination of carrier and therapeutic agent, and the relative concentrations of these materials, can vary depending on the type of lead implanted, the location of lead implantation, the anticipated length of time that the lead is to remain implanted, and rate of elution based on the number and/or size of the elution ports. In one embodiment, the carrier and therapeutic agent can be selected such that the therapeutic agent generally blends well with, and/or is substantially soluble in, the carrier material and/or any solvent in which the therapeutic agent and carrier material are combined prior to insertion into the internal reservoir 42 of the fixation member 30. In embodiments in which extended treatment with a therapeutic agent is desired, it can be desirable to utilize a combination of a carrier and therapeutic agent that provides an extended release of therapeutic agent. In another embodiment, a combination of a carrier and a therapeutic agent that provides an immediate release of the therapeutic agent can be utilized. The release properties of the therapeutic agent can result from the selection of the carrier and/or the therapeutic agent.

Figure 5:
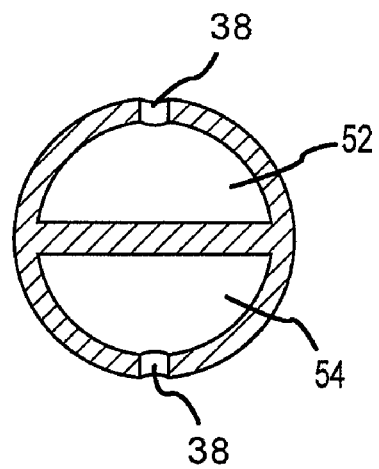
FIG. 5 is a cross section view of the distal end of a cardiac lead according to embodiments of the present invention.

According to certain embodiments of the present invention, the fixation member 30 can include multiple internal reservoirs 42 where each internal reservoir 42 can contain a different therapeutic agent or a different combination of therapeutic agent and carrier. For example, FIG. 5 shows a cross section of the fixation member 30 having two internal reservoirs 52 and 54. The cross section view is taken along line 4-4 of FIG. 4. As illustrated in FIG. 5, the fixation member 30 includes a first internal reservoir 52 and a second internal reservoir 54. In one embodiment, the first internal reservoir 52 and second internal reservoir 54 are substantially parallel to each other along the length of the fixation member 30. In some embodiments the first and second internal reservoirs 52 and 54 can be separated by a physical barrier such as, for example, an internal wall. The first internal reservoir 52 and the second internal reservoir 54 can have different therapeutic agent compositions. The different therapeutic agent compositions have different combinations of therapeutic agent and carrier. Additionally, the different therapeutic agent compositions can have different release times, release rates and/or duration of therapeutic effectiveness depending upon the therapeutic agent and/or carrier that is selected. For example, in one embodiment, the first internal reservoir 52 contains a therapeutic agent composition configured to release an initial burst or bolus of therapeutic agent upon implantation of the lead and the second internal reservoir 54 contains a therapeutic agent composition configured for sustained release of the same or a different therapeutic agent over a period of days, months or even years. Although FIG. 5 shows two internal reservoirs 52 and 54, other embodiments may have three or more internal reservoirs 42.

Figure 6:
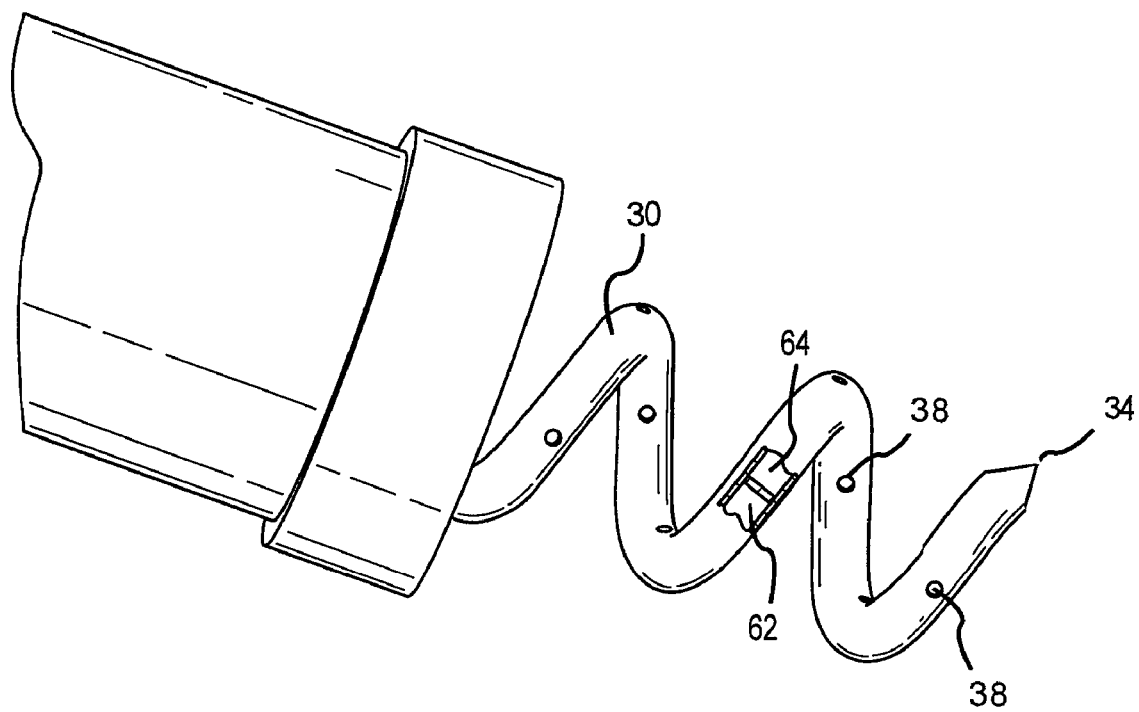
FIG. 6 is a schematic illustration of the distal end of a cardiac lead according to embodiments of the present invention.

In other embodiments of the present invention, the fixation member 30 may have multiple internal reservoirs 42 located in different regions of the fixation member 30 as illustrated in FIG. 6. FIG. 6 illustrates a cut away section of the fixation member 30 with a first internal reservoir 62 and a second internal reservoir 64. As shown in FIG. 6, the first internal reservoir 62 is located within the fixation member 30 at a distance closer to the proximal end of the fixation member 30 while the second internal reservoir 64 is located within the fixation member 30 at a distance closer to the distal end of the fixation member 30. In one embodiment, the first and second internal reservoirs 62 and 64 can be separated by a physical barrier such as, for example, a wall. According to some embodiments of the present invention, the first internal reservoir 62 and the second internal reservoir 64 have different therapeutic agent compositions. In some embodiments, the first and second internal reservoirs 62 and 64 are created by their differing therapeutic agent compositions and have no physical barrier separating them from one another. In various embodiments, the different therapeutic agent compositions have different combinations of therapeutic agent and carrier. Additionally, the different therapeutic agent compositions can have different release times, release rates, or duration of therapeutic effectiveness depending upon the therapeutic agent and/or carrier that is selected. For example, in one embodiment, the first internal reservoir 62 contains a therapeutic agent composition configured to release an initial burst or bolus of therapeutic agent upon implantation of the lead and the second internal reservoir 64 contains a therapeutic agent composition configured for sustained release of the same or a different therapeutic agent over a period of days, months or even years. Although FIG. 6 shows two internal reservoirs 42, other embodiments can have three or more internal reservoirs each having a different therapeutic agent composition.

According to certain embodiments, some of the elution ports 38 are in fluid communication with one internal reservoir 42, while other elution ports are in fluid communication with other internal reservoirs 42. For example, in reference to FIGS. 5 and 6, discussed above, a first set of elution ports 38 can be in communication with a first internal reservoir 52 or 62 and a second set of elution ports can be in communication with a second internal reservoir 54 or 64. The first and second sets of elution ports can vary in number, size, shape, and/or concentration. The configuration and number of the elution ports 38 in communication with a selected reservoir can depend on whether the therapeutic agent composition is designed for an immediate release or an extended release of the therapeutic agent.

According to other embodiments of the present invention, a therapeutic agent can be eluted from within the internal reservoir 42 of the fixation member 30, while a different therapeutic agent can be eluted or otherwise released from a location on the lead 10 adjacent to the fixation member 30.

According to embodiments of the present invention, the therapeutic agent can be delivered to the internal reservoir 42 through pressure injection into the elution ports until the therapeutic agent fills the internal reservoir 42. According to other embodiments of the present invention, the fixation member 30 may have a separate access port to fill the internal reservoir 42 with the therapeutic agent. The separate access port may then be sealed after the therapeutic agent is disposed within the internal reservoir 42. According to other embodiments of the present invention, the therapeutic agent can be disposed within the internal reservoir 42 of the fixation member 30 before the fixation member is coupled (e.g., welded) to the lead 10. According to other embodiments of the present invention, the therapeutic agent can be disposed within the internal reservoir 42 of the fixation member 30 after the fixation member is coupled to the lead 10.

According to embodiments of the present invention, the lead 10 may have a removable sheath over the fixation member 30. For example, the fixation member 30 is covered with the removable sheath during the insertion of the lead into the body, and the fixation member 30 may then be exposed from the removable sheath at the specific fixation site.

FIG. 7 illustrates a flow-chart summarizing a method of providing pace therapy to a patients heart and using embodiments of the present invention. First, a cardiac pacing therapy system is provided. The cardiac pacing therapy system includes a pulse generator and a lead, as described herein.

As illustrated in FIG. 7, the next step for providing pacing therapy to a patient's heart includes affixing the helical fixation electrode to a desired location in the heart such that the elution ports are in close proximity to the site of fixation. The lead 10 of the present invention can be suitable for implantation in the patient's epicardium, endocardium or myocardium. After fixation, the therapeutic agent elutes from the elution ports to treat the fixation site. Pacing therapy is applied to the patient's heart with the pacing therapy system, according to embodiments of the present invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical electrical lead comprising:
   a lead body including a proximal end configured to be coupled to a pulse generator and a distal end adapted to be implanted at an implantation site within a patient's heart;
   at least one conductor extending within the lead body from the proximal end to the distal end;
   at least one electrode located along the lead body and operatively coupled to the at least one conductor;
   a helical fixation member coupled to the distal end of the lead body and configured to engage cardiac tissue at the implantation site, the helical fixation member formed from a hollow tube defining a hollow extending through the hollow tube, an internal wall laterally dividing the hollow into a first internal reservoir in a distal region of the helical fixation member and a second internal reservoir in a proximal region of the helical fixation member, a first plurality of elution ports located along a length of the helical fixation member in fluid communication with the first internal reservoir, a second plurality of elution ports located along a length of the helical fixation member in fluid communication with the second internal reservoir and a sealed distal tip;
   a first therapeutic agent composition comprising a therapeutic agent and a first carrier contained within the first internal reservoir; and
   a second therapeutic agent composition comprising the therapeutic agent and a second carrier contained within the second internal reservoir;
   wherein one of the first and second carriers is selected for rapid release of the therapeutic agent and the other of the first and second carriers is selected for extended release of the therapeutic agent.

2. The medical electrical lead according to claim 1, wherein the therapeutic agent comprises at least one steroid selected from the group consisting of dexamethasone, betamethasone, paramethasone, beclomethasone, clobetasol, trimcinolone, prednisone, prednisolone and derivatives thereof.

3. The medical electrical lead according to claim 1, wherein the therapeutic agent comprises dexamethasone or derivatives thereof.

4. The medical electrical lead according to claim 1, wherein the therapeutic agent comprises beclomethasone or derivatives thereof.

5. The medical electrical lead according to claim 1, wherein the first plurality of elution ports comprises a greater number of elution ports than the second plurality of elution ports.

6. The medical electrical lead according to claim 1, wherein the helical fixation member is electrically active.

7. A medical electrical lead comprising:
   a lead body including a proximal end configured to be coupled to a pulse generator and a distal end adapted to be implanted at an implantation site within a patient's heart;
   at least one conductor extending within the lead body from the proximal end to the distal end;
   at least one electrode located along the lead body and operatively coupled to the at least one conductor;
   a helical fixation member coupled to the distal end of the lead body, the helical fixation member formed from a hollow tube defining a hollow extending longitudinally through the hollow tube, a physical barrier extending across the hollow and laterally dividing the hollow into a first internal reservoir and a second internal reservoir, a plurality of elution portions located along a length of the helical fixation member comprising a first plurality of elution ports in fluid communication with the first internal reservoir and a second plurality of elution ports in fluid communication with the second internal reservoir;
   a first therapeutic agent composition disposed in the first internal reservoir, the first therapeutic agent composition comprising a first steroid disposed in a first carrier to provide an initial burst of the first steroid at the implantation site; and
   a second therapeutic agent composition disposed in the second internal reservoir, the second therapeutic agent composition comprising a second steroid disposed in a second carrier to provide for extended release of the second steroid.

8. The medical electrical lead according to claim 7, wherein the helical fixation member comprises a sealed distal tip configured to engage cardiac tissue.

9. The medical electrical lead according to claim 7, wherein the helical fixation member is operatively coupled to at least one conductor and is electrically active.

10. The medical electrical lead according to claim 7, wherein the first therapeutic agent composition comprises a steroid disposed in a first carrier selected for rapid release of the steroid and the second therapeutic agent composition comprises the steroid disposed in a second carrier selected for extended release of the steroid.

11. The medical electrical lead according to claim 7, wherein the first therapeutic agent composition comprises a first steroid and the second therapeutic agent comprises a second steroid.

12. The medical electrical lead according to claim 7, wherein the first internal reservoir is located in a distal region of the helical fixation member and the second internal reservoir is located in a proximal region of the helical fixation member.

13. The medical electrical lead according to claim 7, wherein the first plurality of elution ports differ in size, shape and/or number from the second plurality of elution ports.

14. The medical electrical lead according to claim 7, wherein the first plurality of elution ports are greater in number than the second plurality of elution ports.

15. The medical electrical lead according to claim 7, wherein the helical fixation member further comprises a third internal reservoir comprising a third therapeutic agent composition disposed therein, wherein a third plurality of elution ports is in fluid communication with the third internal reservoir.

* * * * *